US009233263B2

(12) United States Patent
Gomez-Pamo et al.

(10) Patent No.: US 9,233,263 B2
(45) Date of Patent: Jan. 12, 2016

(54) PHOTOPROTECTOR AND/OR PHOTOIMMUNOPROTECTOR COMPOSITIONS OF THE SKIN AND THEIR USES

(75) Inventors: Antonio Guerrero Gomez-Pamo, Madrid (ES); Marta Dominguez Valdes-Hevia, Madrid (ES); Aurora Ma Brieva Delgado, Madrid (ES); Fernando Garcia Martinez, Madrid (ES); Jose Luis Alonso Lebrero, Madrid (ES); Salvador Gonzalez Rodriguez, Madrid (ES); Juan Pablo Pivel Ranieri, Pozuelo de Alarcon (ES)

(73) Assignee: INDUSTRIAL FARMACEUTICA CANTABRIA, S.A., Santander (ES)

( * ) Notice: Subject to any disclaimer, the term of this patent is extended or adjusted under 35 U.S.C. 154(b) by 0 days.

(21) Appl. No.: 13/317,574

(22) Filed: Oct. 21, 2011

(65) Prior Publication Data

US 2012/0039828 A1  Feb. 16, 2012

Related U.S. Application Data

(63) Continuation of application No. 11/541,350, filed as application No. PCT/ES2004/000149 on Apr. 1, 2004, now abandoned.

(51) Int. Cl.
| A61K 8/35 | (2006.01) |
| A61K 8/36 | (2006.01) |
| A61K 8/365 | (2006.01) |
| A61K 8/60 | (2006.01) |
| A61K 8/67 | (2006.01) |
| A61Q 17/04 | (2006.01) |

(52) U.S. Cl.
CPC . *A61Q 17/04* (2013.01); *A61K 8/35* (2013.01); *A61K 8/36* (2013.01); *A61K 8/365* (2013.01); *A61K 8/60* (2013.01); *A61K 8/678* (2013.01)

(58) Field of Classification Search
CPC ......... A61Q 17/04; A61K 8/365; A61K 8/35; A61K 8/678; A61K 8/60; A61K 8/36
USPC .......................................................... 424/59
See application file for complete search history.

(56) References Cited

U.S. PATENT DOCUMENTS

| 5,298,647 A | 3/1994 | Robert et al. |
| 5,580,549 A | 12/1996 | Fukuda et al. |
| 5,614,197 A * | 3/1997 | Pathak et al. ................. 424/763 |
| 6,235,297 B1 | 5/2001 | Antonelli et al. |

FOREIGN PATENT DOCUMENTS

| EP | 235064 | 9/1987 |
| EP | 570230 | 11/1993 |
| FR | 2390160 | 12/1976 |
| JP | 62036305 | 2/1987 |
| JP | 1013017 | 1/1989 |
| JP | 2003055314 | 2/2003 |
| KR | 98034292 | 8/1998 |
| KR | 98034293 | 8/1998 |
| WO | WO00/74636 | 12/2000 |

OTHER PUBLICATIONS

Brieva, Aurora, Immunomodulatory Properties of a Hydrophilic Extract of Polypodium leucotomos, 2002, Inflammopharmacology, vol. 9, No. 4, pp. 361-371.*
Heliocare Supplement, [online]. Heliocare, 2013, [retrieved Aug. 22, 2013]. Retrieved from the Internet<http://www.treatment-skincare.com/Heliocare/Heliocare-Supplement.html> 2 pages.*
Mimura, M. External Agent for Preventing UV Damage and Rough Skin Contains Tetrahydrocurcumin, JP 06128133, 1994, Derwent Abstract, 2 pages.*
Zandernowski, R, Composition of Phenolic Acids in Sea Buckthorn (*Hippophae rhamnoides* L.) Berries, 2005, Journal of American Oil Chemists' Society, vol. 82, Issue 3, pp. 175-179.
Sea Buckthorn Products: Manufacture and Composition, 1999, Journal of Agricultural Food Chemistry, vol. 47, pp. 3480-3488.
Aggarwal, Bharat, Curcumin-Biological and Medicinal Properties, Jul. 2006, Chapter 10, pp. 297, 321, 322, and 343-346.
Definition of Derivative, Merriam-Webster's Collegiate Dictionary, 1996, 10th Edition.

* cited by examiner

*Primary Examiner* — Sue Liu
*Assistant Examiner* — Andriae M Holt
(74) *Attorney, Agent, or Firm* — Kilpatrick Townsend & Stockton LLP

(57) ABSTRACT

The composition comprises of a component A selected from a hydroxylated derivative of benzoic acid or of cinamic acid, their esters, amides or salts, a glycoside of a hexose, and their mixtures; and a component B selected from quinic acid, shikimic acid, their alkaline metal or alkaline earth salts, their methyl esters, and mixtures of the same. This composition is suitable for protecting the skin against ultraviolet radiation coming from the sun or artificial sources, such as those used in phototherapy units and in sun tanning rooms. For application in the field of dermatology and nutrition, and, in particular, in the photoprotection of the skin and mucosa, photoageing and photocarcinogenesis, including protection of the immune system associated with the skin.

7 Claims, No Drawings

PHOTOPROTECTOR AND/OR PHOTOIMMUNOPROTECTOR COMPOSITIONS OF THE SKIN AND THEIR USES

CROSS-REFERENCE TO RELATED APPLICATIONS

This application is a Continuation of U.S. patent application Ser. No. 11/541,350, filed Sep. 29, 2006, which is incorporated by reference herein.

FIELD OF THE INVENTION

In general, the invention is related to the field of dermatology and photobiology, and, in particular, to the area of photoprotection of the skin and mucosa, including the protection of the immune system associated with the skin. More specifically, the invention is related to a suitable composition to protect the skin against ultraviolet radiation coming from the sun or artificial sources, such as those used in phototherapy units and in sun tanning rooms.

HISTORY OF THE INVENTION

It is becoming increasingly evident that a large number of diseases of the skin are a result of the interaction of ultraviolet (UV) (290-400 nm) and visible (vis) (400-700 nm) radiation on the skin (Gonzalez E, Gonzalez S. Drug photosensitivity, idiopathic photodermatoses and sunscreens. J Am Acad Dermatol 1996; 35: 871-85). In fact, numerous scientific studies suggest that the uncontrolled exposure to solar radiation and ultraviolet radiation coming from artificial lamps is harmful to the human skin and produce burns, damage to the epidermal and dermal cells, induction of cell death, changes in pigmentation, immunosuppression, premature ageing, and, eventually, skin cancer (Young A R. Chronic effects of ultraviolet radiation on the skin. Experimental aspects. In: Dermatology in general medicine: Edited by Fitzpatrick T B, Esen A Z, Wolff K, Freedberg I M, Austen K F. New York. McGraw-Hill Inc., 1993, pp. 1658-1660). While UVB (290-320) radiation is considered the most dangerous component of sunlight as regards the development of acute and chronic skin changes, including skin cancer, UVA (320-400) radiation produces a wide variety of biochemical and biological effects including the generation of reactive oxygen species (ROS), DNA damage, lipid peroxidation, an increase and condensing of the elastic fibres and collagen cross-linking, which leads to changes of the oxidative nature due to photoageing. Therefore the responses of the skin to solar radiation (basically, to radiation in the UV region) are recognised as an inflammatory reaction mediated by several possible mechanisms which include: a) direct action of the photons absorbed by the DNA of the skin cells; b) the generation of ROS and free radicals (for example, superoxide anion ($O_2$), singlet oxygen ($^1O_2$), hydroxyl (OH) or peroxy (OOH) radicals; and c) the synthesis of prostaglandins ($PGD_2$, $PGE_2$), histamines, leukotrienes and cytokines (Black A K, Fircham N, Greaves M W, Hensby C N. Time course changes in levels of arachidonic acid and prostaglandins D2, E2 and F2 alpha in human skin following ultraviolet B radiation. Br J Clin Pharmacol 10: 453-457, 1980; Hawk J M, Black A K, Jaenicke K F, Berr R M, Soter N A, Mallet Al, Gilchrist B A, Hensby C N, Parrish J A, Greaves M W. Increased concentration of arachidonic acid and prostaglandins E2, D2 and 6-oxo-F1alpha, and histamine in skin following UVA radiation. J Invest Dermatol 80: 496-499, 1983; Pentland A P, Needham P. Modulation of keratinocyte proliferation in vitro by endogenous prostaglandin synthesis. J Clin Invest 77: 246-251, 1986; Pentland A P, Jacobs S C. Bradykinin-induced prostaglandin synthesis is enhanced in keratinocytes and fibroblasts by UV injury. Am J Physiol 281:R543-251, 1991; Kupper T S. Role of epidermal cytokines immunophysiology. Edited by Openheim J J, Shervach G M. New York, Oxford University Press, 1990, pp. 285-305; Soter N A. Acute effects of ultraviolet radiation on the skin. Semin Dermatol 9(1): 11-15, 1990; Tedesco A C, Martinez L, Gonzalez S. Photochemistry and Photobiology of actinic erythema. Defensive and reparative cutaneous mechanisms. Braz J Med Biol Res 30:561-575, 1997).

Currently, the most widely accepted method of photoprotection against the damaging effects of UV radiation is based on the topical application of two or more chemical products which act as a topical solar barrier which contains chemical compounds which absorb UVA and UVB radiation and are not photo-labile (for example, octyl methoxycinnamate, octyl dimethylamine-benzoate, benzophenones, or avobenzone (Parsol 1789), etc.), optionally mixed with chemical compounds which disperse and reflect UV radiation (for example, $ZnO_2$, $TiO_2$, in micronised form) incorporated into a base resistant to water (Pathak M A. Sunscreens: Progress and perspectives on photoprotection of human skin against UVB and UVA radiation. J Dermatol 23 (11): 783-800; 1996; Gilaberte Y, Coscojuela C, Saenz de Santamaria M C, Gonzalez S. Photoprotectores. Actas Dermosifiliogr 94(5): 271-293, 2003). The simple topical application of effective sun screens, with a sun protector factor (SPF) between 15 and 30, or higher, can provide reasonable skin protection against the acute harmful effects of UV radiation. Other alternatives include avoiding exposure to sunlight and using tanning lotions, without sun, which contain dihydroxy acetone in combination with chemical compounds which absorb UVB radiation, and chemical compounds with antioxidant properties, such as vitamin C, vitamin E, β-carotene, etc. (Rhodes L E. Topical and systemic approaches for protection against solar radiation induced skin damage. Clin Dermatol 16: 75-82, 1998; Thompson S C, Jolley D, Marks R. Reduction of solar keratoses by regular sunscreen use. N Engl J Med 329 (16): 1147-51, 1993; Gilaberte Y, Coscojuele C, Saenz de Santamaria M C, Gonzalez S. Photoprotectores. Actas Dermosifiliogr 94(5). 271-293, 2003). The presence of effective antioxidants in the skin before exposure to UV radiation can reduce the adverse effects of the radiation, probably by decreasing the generation of ROS induced by the UV radiation (Tedesco A C, Martinez L, Gonzalez S. Photochemistry and Photobiology of actinic erythema. Defensive and reparative mechanisms. Braz J Med Biol Res 30: 561-575, 1997; Dreher F Malbach H. Protective effects of topical antioxidants in humans. Curr Probl Dermatol 29: 157-164, 2001).

Different studies have demonstrated that the repeated systemic administration of antioxidants, such as vitamin C and E, β-carotene, polyphenolic antioxidants, isoflavones, etc. partially inhibit or minimise many cutaneous inflammatory reactions mediated by UV radiation (for example, sun burns, cutaneous phototoxic reactions which involve photosensitisation by drugs, epidermal oedema and vesicle formation) (Darr D, Pinnell S R. Reactive oxygen species and antioxidants protection in photodermatology. Sunscreens. Edited by Lowe N J, Shaat N A, Pathak M A. New York. Marcel Dekker Inc., 1997, pp. 155-173; Green. A, Williams G, Neale R, Hart V, Leslie D, Parsons P, Marks G C, Gaffney P, Battistutta D, Frost C, Lang C, Russell A. Daily sunscreen application and beta-carotene supplementation in prevention of basal cell and squamous cell carcinomas of the skin: a randomised controlled trial. Lancet 354(9180): 723-9, 1999; Stahl W, Heinrich U, Jungmann H, Sies H, Tronnier H. Carotenoids and carotenoids plus vitamin E protect against ultraviolet light induced erythema in humans. Am J Clin Nutr 71: 795-798, 2000). Although these studies in animal experiments have recently been widened to include cosmetic and nutraceutical benefits and therapeutic interventions (for example, in photo-ageing of the skin, in carcinogenesis of the skin), only a few natural antioxidant compounds (for example, polyphenolic antioxidants, silimarine, from Milk Thistle, epigallocatechin-3-gallate, from green tea, lutein and different isoflavones) seem promising in the prevention of damages to the skin induced by UV radiation (Gonzalez S, Astner S, Wu A, Goukassian D, Pathak M A. Oral administration of Lutein modulates cell proliferation induced by acute UVB radiation in the Skh-1 hairless mouse animal model. J Invest Dermatol 121(2): 399-405, 2003; Wang Y, Zhang X, Lebwohi M, DeLeo V, Wei H. Inhibition of ultraviolet B (UVB) induced c-fos and c-jun expression in vivo by a tyrosine kinase inhibitor genistein. *Carcinogenesis* 19(4): 649-654, 1998; Wang Z Y, Huang M T, Lou Y R, Xle J G, Reuhl K R, Newmark H L, Ho C T, Yang C S, Conney A H. Inhibitory effects of black tea, green tea, decaffeinated black tea and decaffeinated green tea on ultraviolet B light induced skin carcinogenesis in 7,12-dimethylbenz [a] anthracene initiated SKH-1 mice. *Cancer Res* 54(13): 3425-3435, 1994; Wai H. Photoprotective action of isoflavone genistein: models, mechanism, and relevance to clinical dermatology. *J Am Acad Dermatol* 39(2 Pt 1): 271-272, 1998).

Besides the recognised direct carcinogenetic effects of UV radiation (Mukhtar H, Elmets C A. Photocarcinogenesis: mechanisms, models and human health implications. Photochem Photobiol 1996: 63; 355-447), it is accepted that the immunosuppression produced by this radiation plays a crucial role in the promotion and development of skin cancer, as well as the higher susceptibility of the skin to different infectious agents (Mukhtar H, Elmets C A. Photocarcinogenesis: mechanisms, models and human health implications. Photochem Photobiol 1996: 83:355-447; Strellen J W, Taylor J R, Vincek V, Kurimoto I, Richardson J, Tie C, Medarna J P, Golomb C. Relationship between ultraviolet radiation-induced immunosuppression and carcinogenesis. J Invest Dermatol 1994; 105 (S):S107-S111; Perna J J, Mannix M L, Rooney J F, Nolkins A L, Straus S E. Reactivation of latent herpes simplex virus infection by ultraviolet light: A human model. J Acad Dermatol 1987; 17:473-8; Jeevan A, Kripke M L. Effect of a single exposure to ultraviolet radiation on Mycobacterium bovis bacillus Calmette-Guerin infection in mice. J Immunol 1989; 143:2837-43; Villarubla V G, Gonzalez S, Cuevas J. Alteraciones inmunologicas inducidas por la radiacion ultrvioleta. Relaciones patogenicas con el fotoenvejecimiento y el cancer de piel. Piel 1996: 11:462-70). This photoimmunosuppression process is basically demonstrated by a reduction in the number of Langerhans cells (Duthie M S, Kimber I, Norval M. The effects of ultraviolet radiation on the human immune system. Br J Dermatol 1999; 140:995-1009; Norval M. Effects of solar radiation on the human immune system. J Photocmem Photobiol B: Biology 2001; 63:28-40) by different mechanisms and which logically lead to slight changes associated with the lower capacity to trap antigens, and with alterations in the processing and presentation of them to the virgin collaborator T lymphocytes in the lymphatic ganglia adjacent to area of irradiated skin. One of the mediators that are considered is urocanic acid (UCA, deaminated histidine), common in the stratum corneum, which is the principal chromophore for the photons of the UV region. UCA is produce by the action of histidase on the histidine amino acid; the absence of urocanase at epidermal level prevents UCA being transformed and the imidazolone compound of propionic acid is produced. Different investigators (Baden H P, Pathak M A. The metabolism and function of urocanic acid in skin. J Invest Dermatol 1987; 45:11-17; Morrison H, Avnir D, Fagan B G. Z/E Photoisomerisation of urocanic acid. Photochem Photobiol 1980; 32:711-714; Morrison H, Panday B G. Urocanic acid Photobiology. Photoaddition of N,N-Dimethylthymine to urocanic acid. Photochem Photobiol 1983; 38:23-27; Finlay-Jones, Hart P H. Ultraviolet irradiation, systemic immunosuppression and skin cancer: role of urocanic acid. Australas J Dermatol 1997; 38 Suppl 1:S7-S12) suggest UCA as a natural solar photoprotector agent, since its absorption spectrum consists of wavelengths from 240 nm to 400 nm (maximum absorption 275 nm) and covers the principal erythematogenic region 290-310 nm. The trans-isomers of UCA present naturally in the skin undergo a photoisomerisation reaction after absorption of photons changing to a cis-isomer, which has been shown to produce many of the immunomodulatory effects of UV radiation (Norval M. Effects of solar radiation on the human immune system. J Photochem Photobiol B; Biology 2001; 63:28-40; Finlay-Jones, Hart P H. Ultraviolet irradiation, systemic immunosuppression and skin cancer: role of urocanic acid. Australas J Dermatol 1997; 38 Suppl 1:S7-S12).

There is, therefore the need to develop efficient photoprotector compositions to prevent or minimise the damaging effects of UV radiation on the skin.

SUMMARY OF THE INVENTION

The invention addresses the problem of providing an efficient composition to prevent or minimise the damaging effects produced by UV radiation on the skin.

The solution provided by the invention is based on the fact that inventors have observed that the combination of a series of components, in determined concentrations, produces a composition which demonstrates an antioxidant and photoprotector effect on the cutaneous cells both in vitro and in vivo, which helps to prevent or minimise the reactions which take place in the skin after a single or repeated exposure to UV radiation. Additionally, the aforementioned composition can be administered topically or orally without losing its photoprotector activity.

Therefore, in one aspect, the invention is associated with a photoprotector and/or photoimmunoprotector composition suitable for preventing or minimising the damaging effects produced by UV radiation on the skin. The aforementioned composition can be used in the preparation of pharmaceutical or cosmetic compositions, as well as food supplements used in the preparation of functional foods.

In another aspect, the invention is associated with an aqueous solution of the aforementioned photoprotector and/or photoimmunoprotector composition adjusted to a pH of between 4.6 and 6.8, preferably between 5 and 6.5 and more preferably between 5 and 5.5.

In another aspect, the invention is associated with a pharmaceutical composition which comprises of the aforementioned photoprotector and/or photoimmunoprotector composition along with one or more pharmaceutically accepted excipients.

In another aspect, the invention is associated with the use of the aforementioned photoprotector and/or photoimmunoprotector composition in the preparation of a drug or pharmaceutical composition to prevent or minimise the damaging effects produced by UV radiation on the skin.

In another aspect, the invention is associated with a cosmetic composition which comprises of the aforementioned photoprotector and/or photoimmunoprotector composition along with one or more cosmetically accepted vehicles.

In another aspect, the invention is associated with a food supplement or a functional food which comprises of the aforementioned photoprotector and/or photoimmunoprotector composition along with one or more acceptable vehicles. These food supplements can be, for example, amino acids, other plant extracts, antioxidant molecules, prebiotic lactic bacterias, yeast for food use, etc. The functional foods can be, for example, milk, cheese, yoghourt, fermented products based on milk, ice creams, products based on fermented cereals, biscuits, fruit juices, cold drinks, plant infusions such as camomile, mint, etc.

In another aspect, the invention is associated with a method to protect the skin in an individual from UV radiation which consists of administering to the aforementioned individual an efficient therapeutic quantity of a photoprotector and/or photoimmunoprotector composition, or an aqueous solution of the aforementioned composition, or of a pharmaceutical composition provided by this invention.

DETAILED DESCRIPTION OF THE INVENTION

In one aspect, the invention provides a composition, from now on the composition of the invention, which comprises of a component A and a component B, where:

(A) aforementioned component A is selected from a group formed by:

A.1) a component A.1 of formula (1)

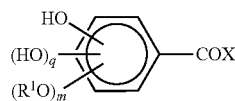
(I)

Where $R^1$ is H or $CH_3$

X represents

OH:

$OR^2$, where $R^2$ is alkyl $C_1$-$C_2$ or the residue of a hydroxylated carboxylic acid of formula

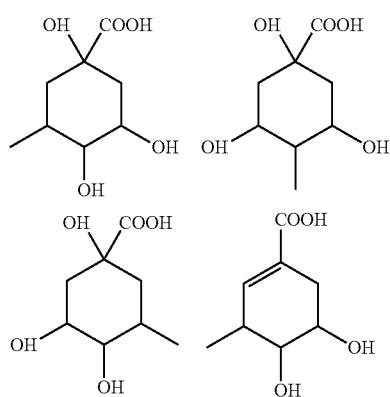

-continued

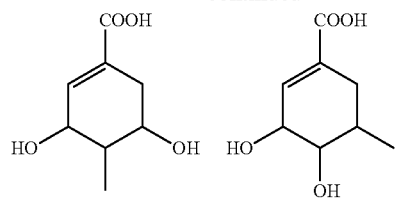

$NH_2$;

m is 0 or 1; y q is 0 or 1: o a salt of the same;

(A.2) a component A.2 of formula (II)

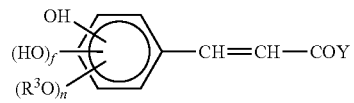
(II)

where $R^3$ is H or $CH_3$;

Y represents

OH;

$OR^2$, where $R^2$ has the previously mentioned significances; or $NH_2$;

n is 0 or 1; y r is 0 or 1; o a salt of the same;

(A.3) a component A.3 of formula (III)

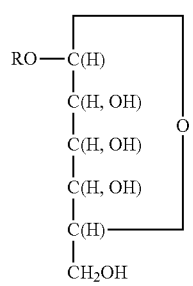
(III)

where R represents (I) a residue of formula (I)

where $R^1$, X, m and q have the previously mentioned significances; or (II) a residue of formula (II)

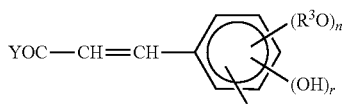

where $R^3$, Y, n and r have the previously mentioned significances;

(A.4) a component A.4 of formula (IV)

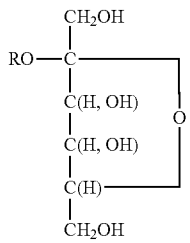

where R has the previously indicated significance;

(A.5) a component A.5 of formula (V)

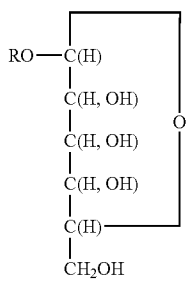

where R has the previously indicated significance; and (A.6) mixtures of the same; and (B) the aforementioned component B is selected from a group made up of quinic acid, shikimic acid, their alkaline metal or alkaline earth salts, their methyl esters and mixtures of the same.

The components A and B can be present in the composition of the invention in a component A:component B ratio of 1-10:1 by weight, for example from 1.6-9.5:1 by weight, from 2-9:1 by weight, from 2.4-7.5:1 by weight, from 2.8.6:1 by weight, from 3.2-5:1 by weight.

The component (A.1) is a hydroxylated derivative (mono-, di-, or trihydroxylated) of benzoic acid (X=OH), an ester (X=OR$^2$), and amide (X=NH$_2$) or a salt of the same. In a particular realisation, X is OR$^2$ where R$^2$ is alkyl $C_1$-$C_2$ or the residue of a hydroxylated carboxylic acid, such as a residue of 1,3,4,5-tetrahydroxycyclohexane-carboxylic acid, for example, of quinic acid [1R-(1α, 3α,4α,5β)-tetrahydroxycyclohexane-carboxylic acid] in any of its configurations, or of 3,4,5-trihydroxy-1-cyclohexane-1-carboxylic acid, for example, shikimic acid [3R-(3α,4α,5β)-3,4,5-trihydroxy-1-cyclohexane-1-carboxylic acid]. In another particular realisation X is NH$_2$. The salts of the hydroxylated derivative of benzoate acid (A.1) include the alkaline metal or alkaline earth salts, for example, sodium, potassium or calcium, preferably, their pharmaceutically acceptable salts. The OH and R$^1$ groups (for their part) can be bound to any of the carbon atoms of the benzene ring with the exception of the carbon atom which is bound to the —COX group.

The (A.2) component is a hydroxylated derivative (mono-, di-, or trihydroxylated) of cinamic acid (Y=OH), an ester (Y=OR$^2$), and amide (Y=NH$_2$) or a salt of the same. In a particular realisation, Y is OR$^2$ where R$^2$ is alkyl $C_1$-$C_2$ or the residue of a hydroxylated carboxylic acid, such as a residue of 1,3,4,5-tetrahydroxycyclohexane-carboxylic acid, for example, of quinic acid, in any of its configurations, or 3,4,5-trihydroxy-1-cyclohexane-1-carboxylic acid, for example, of shikimic acid. In another particular realisation Y is NH$_2$. The salts of the hydroxylated derivative of cinamic acid (A.2) include the alkaline metal or alkaline earth salts, for example, sodium, potassium or calcium, preferably, their pharmaceutically acceptable salts. The OH and R$^2$ groups (for their part) can be bound to any of the carbon atoms of the benzene ring with the exception of the carbon atom which is bound to the chain which contains the carbonyl group. The hydroxylated derivatives of cinamic acid and their derivatives (A.2) have cis-trans isomerism. Any of the isomers, cis, trans or their mixtures, preferably the trans isomer, can be used as component (A.2) in the composition of the invention.

The component (A.3) is a glycoside of an aldohexose, preferably glucose, in any of its configurations (D or L). The R residue corresponds to the residue of formula (I) or the residue of formula (II).

Component (A.4) is a glycoside of a ketohexose, preferably of fructose, in any of its configurations (D or L). The R residue corresponds to the residue of formula (I) or to the residue of formula (II).

The component (A.5) is a glycoside of a 6-deoxyhexose, preferably of rhamnose, in any of its configurations (D or L). The R residue corresponds to the residue of a compound of formula (I) or to the residue of a compound of formula (II).

In general, component A can be made up of one or more components (A.1), or even one or more components (A.2), or one or more components (A.3), or one or more components (A.4), or one or more components (A.5), or even any mixture of two or more of the aforementioned components (A.1) to (A.5), where each one of the components A.1 to A.5 can be composed of, for their part, by one or more compounds of the same group. However, in a particular realisation, component A comprises of (i) at least two different components (A.1), and (ii) at least two different components (A.2). In this case the component (A.1):component (A.2) molar ratio is between 0.5 and 2.

Component B is selected from a group made up of quinic acid, shikimic acid, their alkaline metal or alkaline earth salts, their methyl esters, and mixtures of the same. In general quinic or shikimic acid, and their derivatives (salts and esters) have the same free hydroxyl groups. Quinic acid and its derivatives have optical stereoisomerism. Any of the isolated optical stereoisomers, as well as their mixtures, can be used in the composition of the invention. Shikimic acid and its derivatives have optical stereoisomerism. Any of the isolated optical stereoisomers, as well as their mixtures, can be used in the composition of the invention.

In a particular realisation of the invention, component B is selected between quinic acid, in any of its possible configurations (D or L) in the carbon 1 atom (C1), a salt of an alkaline metal or alkaline earth, for example, sodium, potassium or calcium, of the aforementioned quinic acid, a metal ester of shikimic acid, and mixtures of the same. In another particular realisation, component B is selected between shikimic acid, a salt of an alkaline metal or alkaline earth, for example, sodium, potassium or calcium, of the aforementioned shikimic acid, a metal ester of shikimic acid, and mixtures of the same. In another particular realisation, component B comprises of a mixture of the aforementioned quinic acid and/or its derivatives (salts or esters) and the aforementioned shikimic acid and/or its derivatives (salts or esters).

If desired, the composition of the invention, besides component A and B, can also contain one or more components selected from a group made up of Component C, component D, component E, component F and their mixtures, where:

said component C is selected from the group made up of:

(C.1) component C.1 of the formula (VI)

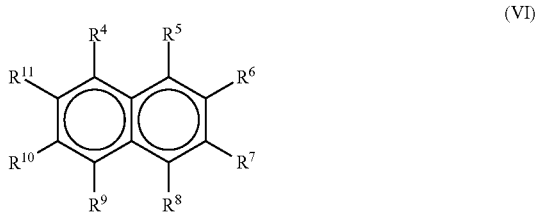

(VI)

where $R^4$, $R^5$, $R^6$, $R^7$, $R^8$, $R^9$, $R^{10}$, and $R^{11}$, equal or different, independent of each other, represent H, OH, $OR^5$, —CH=CH—COY, or —COY where $R^5$ and Y have the significances previously mentioned, or a salt of the same, with the condition that (i) at least two of $R^4$, $R^5$, $R^6$, $R^7$, $R^8$, $R^9$, $R^{10}$, or $R^{11}$ are, simultaneously, OH, (ii) one of $R^4$, $R^5$, $R^6$, $R^7$, $R^8$, $R^9$, $R^{10}$, or $R^{11}$ is $OR^3$, (iii) the maximum number of hydroxyl groups present is 3, and (iv) one of $R^4$, $R^5$, $R^6$, $R^7$, $R^8$, $R^9$, $R^{10}$, or $R^{11}$ is —CH=CH—COY or —COY;

(C.2) component C.2 of formula (VII)

(VII)

where $R^6$ represents H or a OH, $OR^3$, or —CH=CH—COY group where $R^3$ and Y have the significances previously mentioned, or a salt of the same;

(C.3) component C.3 of formula (VIII)

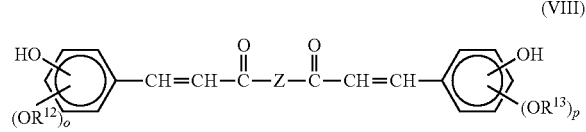

(VIII)

where $R^{12}$ and $R^{13}$, equal or different, independently of each other, represent H or $CH_3$;

Z represents —$CH_2$—, O, S or NH;

o is 0 or 1; and p is 0 or 1, and (C.4) their mixtures;

aforementioned component D is selected between one or more free monosaccharides;

aforementioned component E is selected from the group made up of an acid of the Krebs cycle, an alkaline metal or alkaline earth salt of an acid of the Krebs cycle, a mono-, di-, or trimethyl ester of an acid of the Krebs cycle, aldaric acid, a salt or alkaline or alkaline earth metal salt of aldaric acid, a lactone derivative of aldaric acid, aldonic acid, an alkaline metal or alkaline earth salt of aldonic acid, a lactone derivative of aldonic acid, or mixtures of these compounds; and aforementioned component F is selected from a group made up of a water soluble vitamin, a water soluble derivative of a lipid soluble vitamin, and their mixtures.

Component C, is selected from a group made up of component (C.1), (C.2), (C.3) and their mixtures, in the case of being present in the composition of the invention, it could be present in a quantity of between 0.1% and 10% by weight as regards the total composition of the invention, preferably, between 0.5% and 5%.

Component (C.1.) is a derivative of 3-[(di- or tri)hydroxynaphthyl)-2-ene-propanoic acid (Y=OH), an ester (Y=$OR^2$), an amide (Y=$NH_2$) or a salt of the same, or a derivative of 3-(di- or tri)hydroxynaphthoic acid (Y=OH), an ester (Y=$OR^2$), an amide (Y=$NH_2$) or a salt of the same. In a particular realisation, Y is $OR^2$ where $R^2$ is an alkyl $C_1$-$C_2$ or the residue of a hydroxylated carboxylic acid, such as the residue of 1,3,4,5-tetrahydroxycyclohexane carboxylic acid, for example of quinic acid, in any of its configurations, or 3,4,5-trihydroxy-1-cyclohexane-1-carboxylic acid, for example, of shikimic acid. In another realisation Y is $NH_2$. The salts of the derivative of 3-[(di- or tri)hydroxynaphthyl)-2-ene-propanoic acid or the derivative of 3-(di- or tri)hydroxynaphthoic acid (C.1) include the salts of the alkaline or alkaline earth metals, for example sodium, potassium or calcium, preferably, pharmaceutically acceptable salts of the same. The OH and $OR^2$ groups (for their part) can be bound to any of the carbon atoms of the benzene ring with the exception of the carbon atom which is bound to the chain which contains the group —CH=CH—COY or —COY. The hydroxylated derivatives of 3-[(di- or tri)hydroxynaphthyl)-2-ene-propanoic acid or the derivative of 3-(di- or tri)hydroxynaphthoic acid (C.1) have cis-trans isomers. Any of the cis, trans isomers or their mixtures, preferably the trans isomers can be used as component (C.1) in the composition of the invention.

Component (C.2) is a derivative of 3-(hydroxyimidazolyl)-2-ene-propanoic acid (Y=OH), an ester (Y=$OR^2$), an amide (Y=$NH_2$) or a salt of the same. In a particular realisation, Y is $OR^2$ where $R^2$ is an alkyl $C_1$-$C_2$ or the residue of a hydroxylated carboxylic acid, such as the residue of 1,3,4,5-tetrahydroxycyclohexane carboxylic acid, for example of quinic acid, in any of its configurations, or 3,4,5-trihydroxy-1-cyclohexane-1-carboxylic acid, for example, of shikimic acid. In another realisation Y is $NH_2$. The salts of the derivative of 3-(hydroxyimidazolyl)-2-ene-propanoic acid (C.2.) include the salts of the alkaline or alkaline earth metals, for example sodium, potassium or calcium, preferably, pharmaceutically acceptable salts of the same. The hydroxylated derivatives of 3-(hydroxyimidazolyl)-2-ene-propanoic acid (C.2.) have cis-trans isomers. Any of the cis, trans isomers or their mixtures, preferably the trans isomers can be used as component (C.2) in the composition of the invention.

Component (C.3), depending on the significance of Z, can include a —CH2-, 0, S, or NH group. The compounds of formula (VIII) [component (C.1)] contains two double bonds, therefore they have two cis-trans isomer centres. Any of the possible isomers (cis-cis, cis-trans, trans-cis and trans-trans isomers), preferably, the trans-trans isomers, can be used as (C.3) component in the composition of the invention.

In general, the C component can be made up of one or more different components (C.1), or by one or more different (C.3) components, or by mixtures of one or more (C.1) and (C.2) components, or by mixtures of one or more (C.2) and (C.3) components, or by mixtures of one or more (C.1), (C.2) and (C.3) components. However, in a particular realisation, component C comprises of at least a (C.3) component. The presence of the C component in the composition of the invention could reinforce or increase its photoprotector activity.

Component D, in case it is present in the composition of the invention, could be present in an amount comprising between 35% and 90% by weight in respect to the total composition of the invention, preferably between 45% and 65%. Component D provides a physiological reductor medium which favours the stabilisation of the molecules of components A and/or C (for their part).

Component D comprises of one or more free monosaccharides, in any of their configurations. In a particular realisation, component D is selected from glucose, rhamnose and fructose, in any of their possible configurations.

Component E, in case it is present in the composition of the invention, could be present in an amount comprising between 5% and 30% by weight in respect to the total composition of the invention, preferably between 10% and 20%. Component E provides a decrease in the pH which favours the stability of the invention.

Component E can be made up of one or more acids of the Krebs cycle, for example, citric, isocitric, α-oxoglutaric, succinic, fumaric, malic or oxaloacetic acid, preferably, citric acid, fumaric or malic, and/or by one or more of their alkaline metal or alkaline earth salts, for example, sodium, potassium or calcium and/or one or more of their mono-, di-, or tri-metallic esters. Alternatively, the said component E can be made up of (i) an aldaric acid, that is to say, a polyhydroxylated dicarboxylic acid, optionally unsaturated, coming from an aldose by oxidation of the carbon atoms of the ends of the aldose to the carboxylic groups, or one of its alkaline metal or alkaline earth salts, for example, sodium, potassium or calcium, or their corresponding lactonised forms, or their mixtures, and/or by (ii) an aldonic acid, that is to say, a polyhydroxylated dicarboxylic acid, optionally unsaturated, coming from an aldose by oxidation of the aldehyde function, or one its alkaline metal or alkaline earth salts, for example, sodium, potassium or calcium, or their corresponding lactone forms, or their mixtures. Among the aldaric acids which can, eventually, be present in the composition of the invention are the aldaric acids with 5 and 6 carbon atoms, for example, xilaric, glucaric, galactaric acid, etc., optionally in the form of an alkaline metal or alkaline earth salt, or in one of its lactone forms, for example, 3-oxo-L-gulofuranolactone, etc. Among the aldonic acids which can, eventually, be present in the composition of the invention are the aldonic acids with 5 and 6 carbon atoms, for example, xilonic, gluconic acid, etc., optionally in the form of an alkaline metal or alkaline earth salt, or in one of its lactone forms, for example, D-glucone-1,4-lactone, D-glucone-1,5-lactone, etc.

Component E can, therefore, be made up of one or more acids from the Krebs cycle, preferably, citric, fumaric or malic acid, and/or one or more of their and/or by one or more of their alkaline metal or alkaline earth salts, for example, sodium, potassium or calcium and/or one or more of their mono-, di-, or tri-metallic esters, and/or by one or more aldaric acids, and/or by one or more aldonic acids, and or one or more alkaline metal or alkaline earth salts of these aldaric and/or aldonic acids, and/or by one or more aldaric acids and/or aldonic acids in their lactone forms.

Component F, in case it is present in the composition of the invention, could be present in a quantity of between 4% and 20%, preferably, between 6% and 12% by weight in respect of the total of the composition of the invention. Component F has an anti-radical effect which favours the stability of the mixture and complements the anti-radical defences of the body.

Component F can be made up of one or more water soluble vitamins, such as ascorbic acid and or one or more water soluble derivatives of lipid soluble vitamins, such as alpha-carotene, beta-carotene, zeaxanthin, lutein, lycopene, alpha-tocopherol, etc. In a particular realisation, component F comprises of a water soluble vitamins, such as ascorbic acid (vitamin C) or a water soluble derivative of a lipid soluble vitamin, such as a water soluble derivative of tocopherol (Trolox) or a mixture of such water soluble vitamins and water soluble derivatives of lipid soluble vitamins. Vitamin C and/or the water soluble derivatives of vitamin E act as stabilisers and antioxidant agents of the composition of the invention.

The combination of components A and B constitute the photoprotector base of the composition of the invention. Component C, for its part, appears to reinforce or increase the photoprotector activity of the combination of components A and B. The absence of stabilising additives and/or preservatives could cause a significant reduction of the average life of the composition of the invention. For this reason, in a particular realisation of the invention, the composition of the invention includes an additive, such as a preserving and/or stabilising agent, which contributes to increasing the average life of the composition of the invention to maintain its photoprotector properties for a longer time. In this way, the photoprotector activity of the composition of the invention would be more efficient by being more stable and would remain active for a longer time. Illustrative examples of these additives include compounds which contribute to the stability of the composition of the invention due to their reducing power (component D) or their acidity (component E). The addition of vitamins or their derivatives with preservative and/or anti-oxidant applications (component F) also contribute to stabilising and preserving the composition of the invention.

The composition of the invention includes any possible combination of the different components. In a way of illustration, the composition of the invention, includes the following combinations of components:

component A+component B,
component A+component B+component C,
component A+component B+component D,
component A+component B+component E,
component A+component B+component F,
component A+component B+component C+component D,
component A+component B+component C+component E,
component A+component B+component C+component F,
component A+component B+component D+component E,
component A+component B+component D+component F,
component A+component B+component E+component F,
component A+component B+component C+component D+component E,
component A+component B+component C+component D+component F,
component A+component B+component D+component E+component F,
and
component A+component B+component C+component D+component E+component F.

A class of compositions of the invention includes the binary mixtures of component A and B where the ratio of component A:component B is 1-10:1 by weight. In a particular realisation, the invention provides a binary composition composed of 65-90% by weight of component A and 35-10% by weight of component B, preferably, between 74-88% by weight of component A and between 28-14% by weight of component B.

Another class of combinations of the invention includes ternary mixtures made up of components A and B and a third component selected between component C, component D, component E and component F. The quantity of component C, D, E or F present in these compositions is that mentioned previously to define these components and the rest constitutes the mixture of components A and B in the weight ratio defined previously.

Another class of compositions of the invention includes quaternary mixtures made up of components A and B and two other components selected between components C, D, E, and F. Among the quaternary compositions provided by this invention, the composition formed by components C, D, E, and F constitute a preferred composition of the invention. In a particular realisation, the invention provides a quaternary composition made up of 5-35% by weight of component A+component B, where the ratio of
component A:component B is 1-10:1 by weight;
35-90% by weight of component D; and
5-30% by weight of component E.

An additional class of compositions of the invention includes mixtures of five components formed by components A and B and three other components selected from components C, D, E, and F. Among the compositions of five components provided by this invention, the composition made up of components A, B, D, E and F constitute a preferred composition of the invention. In a particular realisation of, the invention provides a composition of five components made up of 5-35% by weight of component A+component B, where the ratio of
component A:component B is 1-10:1 by weight;
30-85% by weight of component D;
5-20% by weight of component E; and
5-15% by weight of component F.

Finally, another additional class of compositions of the invention includes mixtures of six components formed by components A, B, C, D, E, and F. In a particular realisation, the invention provides a composition of five components made up from 5-30% by weight of component A+component B, where the ratio of component A:component B is 1-10:1 by weight;
1-5% by weight of component C;
30-84% by weight of component D;
5-20% by weight of component E; and
5-15% by weight of component F.

The composition of the invention can be in solid phase or in liquid phase. In a particular realisation, the composition of the invention is in the liquid phase, typically, in the form of an aqueous solution with a pH between 4.8 and 6.8, by means of the addition of an acid or basic pH adjusting agent, depending on the process.

The composition of the invention can be obtained by a conventional procedure which consists of mixing the different components in the appropriate amounts. In a particular realisation, the composition of the invention is in the form of an aqueous solution with a pH between 4.8 and 6.8, preferably, between 5 and 6.5. This aqueous solution of the composition of the invention can be obtained using a procedure which consists of weighing the different compounds, measuring an appropriate quantity of water, preferably distilled or deionised, heated to a temperature of between 37° C. and 55° C., mixing gently to avoid solubilising the oxygen, leaving the composition to cool to ambient (room) temperature and adjusting the pH to between 4.8 and 6.8, preferably between 5 and 6.5, by the addition of a pH adjusting agent. The pH adjusting agent can be an organic or inorganic acid, for example, acetic acid, hydrochloric acid, etc., or an organic or inorganic bases, for example, sodium hydroxide, etc., capable of providing the desired pH of the composition of the invention. The composition obtained is filtered and stored in suitable conditions, for example, at a temperature equal to or lower than −20° C. The addition order of the components can vary depending on, among other factors, the nature and composition of the different components used in the preparation of the composition of the invention. On occasions it can be necessary to add a surfactant and/or chelating agent to help in the preparation of the composition of the invention.

The composition of the invention has antioxidant capacity, determined using the FRAP method (see Example 1.2) and is capable of significantly blocking the photoisomerisation of urocanic acid (UCA) induced by UV radiation (see Example 1.4). The aforementioned composition of the invention also exercises an in vitro photoprotector effect on keratinocytes and fibroblasts subjected to severe UV radiation, such as has been demonstrated by carrying out in vitro studies of cell survival and proliferation with fibroblasts and keratinocytes (see Example 1.3) and an unexpected in vivo photoprotector effect by inhibition of the immunosuppressor effect induced by ultraviolet radiation in a mouse model of contact hypersensitivity to oxazolone (see Example 1.5). Therefore, the composition of the invention can be used in therapeutic applications, in human or animal health, in the field of dermatology, photomedicine and photobiology, and, in particular, in the photoprotection, photoimmunoprotection and protection of the skin. More specifically, the composition of the invention can be used to protect the skin against the harmful effects of ultraviolet radiation coming from the sun or artificial sources, such as those used in phototherapy units or sun tanning rooms. In a way of illustration, the composition of the invention can be used in (1) the prevention of cutaneous immunosuppression which occurs after exposure to the sun or UV coming from an artificial source, which would facilitate the appearance of secondary infections and the promotion of skin cancer, (2) as an adjuvant agent in phototherapy (phototherapy with UVB, PUVA (psoralens plus UVA, that is to say, therapy where an individual is sensitised by administering psoralens and is irradiated with UVA radiation) of chronic diseases, such as psoriasis and vitiligo, preventing some of the harmful effects of the radiation without affecting its therapeutic efficacy, (3) in subjects susceptible to skin cancer during inevitable exposure to the sun, such as very obvious skin phototype subjects (Fitzpatrick phototypes I and II), subjects with a previous history of skin cancer in the form of actinic keratosis, basal cell and spinal cell carcinomas and melanoma, subjects on treatment with systemic photosuppressor agents, subjects with genetic abnormalities which favour the appearance of skin cancer (pigmentous xeroderma), (4) in subjects with idiopathic photodermatosis (polymorph luminal eruption, solar urticaria, chronic actinic dermatitis, etc.), (5) in subjects with skin photosensitisation due to the ingestion of chemical substances (tetracyclines, amiodarone, phenothiazines, quinolones, non-steroidal anti-inflammatory drugs, etc.).

Therefore, in another aspect, the invention is associated with a pharmaceutical composition which comprises of a therapeutically efficient quantity of the composition of the invention together with, at least, one pharmaceutically accepted excipient. This pharmaceutical composition is useful for its administration and/or application on the body of an animal, such as a mammal, preferably a human being.

The use of the composition of the invention in the preparation of the aforementioned pharmaceutical composition constitutes an additional aspect of this invention.

The composition of the invention can be administered to protect the skin from ultraviolet radiation by whatever means that brings the composition of the invention in contact with the site of action of the same in the body of the animal.

The therapeutically effective quantity of the composition of the invention which has to be administered, as well as the dosing to treat a pathological state with the composition of the invention, will depend on many factors, including age, state of the patient, the severity of the changes or disorder, the route and frequency of administration, the composition of the invention to use, etc.

The pharmaceutical compositions which contain the composition of the invention can be in any form of administration, for example, solid or liquid, and can be administered, orally, sublingually, parenterally or topically, preferably orally, sublingually or topically, more preferably orally, therefore, it will include the pharmaceutically acceptable excipients necessary for the formulation of the desired administration form. A review of the different pharmaceutical forms of administering drugs and the excipients necessary to obtain them can be found, for example, in the "Tratado de Farmacia Galenica", C. Faull I Trillo, 1993, Luzan 5, S.A. Ediciones, Madrid.

In another aspect, the invention is associated with the use of the composition of the invention in the preparation of a drug or pharmaceutical composition to protect the skin from the harmful effects of ultraviolet radiation; in particular, (1) in the prevention and/or treatment of cutaneous immunosuppression which occurs after sun or UV exposure coming from an artificial source which facilitates the appearance of secondary infections and the beginning or promotion of skin cancer, (2) as an adjuvant agent in phototherapy of chronic diseases, such as psoriasis and vitiligo, preventing some of the harmful effects of the radiation without affecting its therapeutic efficacy, (3) as a skin protector in subjects susceptible to skin cancer during inevitable exposure to the sun, (4) in subjects with idiopathic photodermatosis (polymorph luminal eruption, solar urticaria, chronic actinic dermatitis, etc.), (5) in subjects with skin photosensitisation due to the ingestion of chemical substances and drugs, etc.

In another aspect, the composition of the invention could be used in the preparation of a cosmetic composition with the aim of protecting the skin from the harmful effects of ultraviolet radiation coming from the sun or sources of UV radiation, such as those used in phototherapy units or in sun tanning rooms.

Therefore, the invention is also associated with a cosmetic composition which comprises of the invention together with one or more therapeutically acceptable excipients. The cosmetic composition provided by this invention can be applied topically. Therefore, in a particular realisation, the invention provides a cosmetic composition, for its topical application, which comprises of the composition of the invention together with one or more cosmetically acceptable suitable excipients. A review on cosmetics and excipients necessary for obtaining them can be found in, for example, in "Cosmetologia Teoretico-Practica", published by the General Council of the Official Pharmacy Colleges, $3^{rd}$ Edition (1985). The aforementioned cosmetic composition can be in any application form by a topical route which is appropriate, for example, creams, gels, emulsions, lotions, milks, oils, etc., as pre-sun as well as after-sun.

In another aspect, the invention is associated with a food supplement or functional food which comprise of the aforementioned photoprotector and/or photoimmunoprotector composition together with one or more acceptable vehicles. These food supplements can be, for example, amino acids, plant extracts, antioxidant molecules, prebiotic lactic bacteria, yeasts for food use, etc., or mixtures of the same. In a way of an example, the functional foods can have milk, cheese, yoghourt, milk based fermented products, ice creams, products based on fermented cereals, biscuits, fruit juices, cold drinks, plant infusions such as camomile, etc.

In another aspect, the invention is associated with a method to protect the skin of an individual from UV radiation which comprises of administering to that individual an efficient therapeutic quantity of a photoprotector and/or photoimmunoprotector composition provided by this invention, or the aforementioned aqueous solution adjusted to a pH between 4.8 and 6.8 of the photoprotector and/or photoimmunoprotector composition provided by this invention.

The following example illustrates the invention and must not be considered limiting the scope of the invention.

Example 1

Photo (Immune) Protector Compositions and their Properties 1.1 Photo (Immune) Protector Compositions The compositions 1-VI which are shown in Table 1 are prepared by means of measuring and mixing of the different compounds up to homogenisation, adjusting the pH to the values indicated by means of the addition of sodium hydroxide.

TABLE 1

| | | Prepared compositions | | | | | |
| --- | --- | --- | --- | --- | --- | --- | --- |
| | Component | I | II | III | IV | V | VI |
| A | 4-hydroxy benzoic acid | 0.128 g | 0.128 g | 0.128 g | — | 0.128 g | — |
| A | 3,4-dihydroxybenzoic acid | 0.112 g | 0.112 g | 0.112 g | 0.112 g | 0.112 g | 0.112 g |
| A | 3-methoxy-4-hydroxybenzoic acid | 0.096 g | 0.096 g | 0.096 g | 0.096 g | 0.096 g | 0.096 g |

TABLE 1-continued

| | | Prepared compositions | | | | | |
|---|---|---|---|---|---|---|---|
| | Component | I | II | III | IV | V | VI |
| A | 4-hydroxycinamic acid | 0.096 g | 0.096 g | 0.096 g | 0.096 g | 0.096 g | 0.096 g |
| A | 3,4-dihydroxycinamic acid | 0.096 g | 0.096 g | 0.112 g | 0.096 g | 0.096 g | 0.096 g |
| A | 3-methoxy-4-hydroxycinamic acid | 0.016 g | 0.016 g | 0.033 g | 0.106 g | — | — |
| A | Chlorogenic acid | 0.006 g | 0.006 g | — | 0.223 g | 0.06 g | 0.223 g |
| A | Amide of 3,4-dihydroxycinamic acid | — | 0.1 g | — | — | — | — |
| B | Quinic acid[a] | 0.150 g | 0.150 g | 0.200 g | 0.130 g | 0.150 g | 0.130 g |
| C | Curcumin | — | — | — | — | 0.032 g | 0.201 g |
| pH[b] | | 5.5 | 6.5 | 5.5 | 6.5 | 5.5 | 6.5 |
| Administration | | Oral | Topical | Oral | Topical | Oral | Topical |

[a]1,3,4,5-tetrahydrocyclohexanonecarboxylic acid
[b]The pH is adjusted with NaOH Additionally, mixtures of additional components were prepared, identified as 1, 2, 3 in Table 2, and they were added to compositions I-VI, giving rise to the compositions named I-1, I-2, I-3, II-1, II-2, II-3, III-1, III-2, III-3, IV-1, IV-2, IV-3, V-1, V-2, V-3, VI-1, VI-2, and VI-3, where the Roman numeral indicates the composition and the Arabic figures indicate the additional components. The pH values of the resulting compositions were adjusted to 5.5 or 6.5 with the addition of NaOH depending on the particular composition I-VI used.

TABLE 2

| | Mixtures of additional components | | | |
|---|---|---|---|---|
| | Component | 1 | 2 | 3 |
| D | Fructose | 0.7 g | 0.7 g | 0.7 g |
| | Glucose | 1.7 g | 1.7 g | 1.7 g |
| | Mannose | 0.05 g | 0.05 g | 0.05 g |
| E | Citric acid | 0.16 g | 0.16 g | 0.16 g |
| | Citrate | 0.51 g | 0.5 g | 0.5 g |
| | Malic acid | 0.09 g | 0.09 g | — |
| | Fumaric acid | — | — | 0.04 g |
| | Gluconic acid | — | — | 0.07 g |
| | 3-oxo-gulofuranolactone | — | 0.04 g | — |

1.2 Determination of the Antioxidant Capacity

The antioxidant capacity of the previously described composition was determined using an in vitro assay known as the "FRAP method".

The FRAP (ferric-reducing ability of plasma, or the capacity of plasma to reduce the ferric cation) is a colorimetric redox method with a high reproducibility and sensitivity, by which a change in absorbance at 593 nm is monitored, which signifies a ferric-ferrous redox process (Benzie I. J and Strain J J. Methods in Enzymology, vol 299: Oxidants and antioxidants, Part A (1999).

Composition and preparation of the FRAP solution (prepared in the laboratory):
  Acetate buffer: 300 mM sodium acetate trihydrate pH 3.6 (3.1 g of sodium acetate)+16 ml glacial acetic acid and make up to 1 L with distilled water.
  TPTZ: 10 mM of 2,4,6-tripyridyl-s-triazine in 40 mM HCl (2.27 mL of 37% HCl in 100 mL of Milli-Q water (10 mM TPTZ=0.312 g/100 mL of 40 mM HCl).
  Ferric chloride: 20 mM ferric chloride hexahydrate (0.541 g/100 mL of pH 3.6 acetate buffer).
  Mix the three solutions beforehand in a ratio of 10:1:1 for the FRAP reagent: Keep the mixture at 37° C. during the test.

Briefly, 3 mL of FRAP reagent and 150 uL of sample under test (1 mg/mL) or control are mixed in a test tube. It is mixed and the absorbance is measured at 593 nm along with a positive and negative control. The reaction is carried out for 300 seconds at 37° C.

The results are calculated according to the following formula:

$$\% \text{ FRAP (w/w)} = 100 \times [(A_{rel\ 300\ secs})_{sample} \times [\text{trolox}]/(A_{rel\ 300\ sec})_{Trolox} \times [\text{sample}]]$$

where $(A_{rel\ 300\ secs})_{sample}$ is the relative absorbance of the sample at 300 seconds.

$(A_{rel\ 300\ sec})_{trolox}$ is the relative absorbance of the Trolox at 300 seconds.

The results obtained showed that a quantity of 1 mg/mL of compositions I-1, I-2, I-3, II-1, II-2, II-3, III-1, III-2, III-3, IV-1, IV-2, IV-3, V-1, V-2, V-3, VI-1, VI-2, and VI-3, included within the field of the invention, had a high antioxidant capacity, of the order of 40-80% vs 100% of the antioxidant capacity of the Trolox (reference molecule), that is to say, of the same order of magnitude as that of an isolated and pure molecule, as the Trolox is, (the antioxidant capacity of the Trolox in the conditions tested is taken as a reference and the analysis of the antioxidant activity sample is a percentage of the value of 100 which is assigned to the antioxidant activity of the Trolox) [Trolox] molecule of reference: derived from water soluble vitamin E: (R)-(+)-6-hydroxy-2,5,7,8-tetramethylchroman-2-carboxylic acid. (Sigma Chemicals Ltd)].

1.3 Survival and Proliferation of Irradiated Human Keratinocytes and Fibroblasts The photoprotector effect of the compositions provided by this invention has been determined in two in vitro assays of cell survival and proliferation with fibroblasts and keratinocytes, cells present in the skin and therefore exposed to solar UV radiation which reaches the surface of the earth. In both tests, the compositions provide by this invention demonstrated, against a severe ultraviolet challenge, a photoprotector effect which enabled the functional structure of the cell population to be maintained and that this proliferated at a pace near to that of the non-irradiated control cells, ruling out their disappearance by apoptosis as well as their cell hyperproliferation characteristic of tumour cells.

1.3.1 Cell Survival of Human Keratinocytes Irradiated with Ultraviolet Light The photoprotector effect of the compositions provided by the invention was determined in human keratinocyte cultures in survival tests in the presence of UV radiation.

Briefly, single layers of human keratinocytes from HaCat cell line (Boulcamp P, Pertussovska R T, Breitkreuss D, Hornung J, Markham A, Fusenig N E. J Cell Biol. 1988, 106: 761-771), were washed twice with PBS (phosphate buffered saline) and irradiated in the presence of the composition of the invention at different determined doses in each experiment. The UVA radiation exposure doses were supplied in $J/cm^2$ (generally 5 $J/cm^2$), while the doses of UVB radiation were supplied in $mJ/cm^2$ (generally 500 $mJ/cm^2$). Next, they were cultivated in a complete culture medium. DMEM supplemented with 10 U/mL of penicillin-streptomycin, 10 mM glutamine and 10% foetal calf serum (all reagents from Sigma) and the cultures were incubated at 37° C. in a $CO_2$ atmosphere of 5% until the samples were analysed (3 hours after the irradiation).

Cell survival is calculated by measuring the mitochondria dependent conversion of the tetrazolium salt MTT (Sigma) in a coloured formazan product. The cells were treated as has been indicated previously and, then the MTT compound (0.5 mg/mL) was added to each well and the resultant mixtures were incubated at 37° C. for 2 h. Next, the medium was carefully aspirated and 200 uL of acidified isopropyl alcohol were added to solubilise the coloured formazan product. The absorbance was read at 550 nm in a multi-well beam spectrophotometer after vigorously mixing the plates for 5 minutes.

The results obtained demonstrated that a quantity of 1 mg/mL of compositions I-1, I-2, I-3, II-1, II-2, II-3, III-1, III-2, III-3, IV-1, IV-2, IV-3, V-1, V-2, V-3, VI-1, VI-2, and VI-3, included within the field of the invention, increased the cell survival in 70-80% of the cells exposed to UVA radiation intensities of 5 $J/cm^2$. The capacity of some of these compositions of the invention to improve the survival of human keratinocytes after UVA radiation (5 $J/cm^2$) or UVB (0.5 $J/cm^2$), using HaCat human keratinocytes cell line is shown in Table 3.

TABLE 3

Survival of human keratinocytes (% with respect to the non-radiated baseline cells), after UVA or UVB radiation.

| Composition | UVA | UVB |
| --- | --- | --- |
| I-1 | 86 ± 2 | 75 ± 3 |
| II-2 | 80 ± 3 | 70 ± 4 |
| III-3 | 82 ± 3 | 71 ± 3 |
| IV-1 | 82 ± 3 | 74 ± 3 |
| V-2 | 85 ± 4 | 77 ± 2 |
| VI-3 | 83 ± 2 | 73 ± 2 |
| Irradiated control | 40 ± 4 | 30 ± 4 |

[Control: Cells irradiated with ultraviolet light, without treatment (the cells were used as they were)

1.3.2 Proliferation of Human Fibroblasts Irradiated with Ultraviolet Light

Human fibroblasts obtained from human donors were used which were cultivated in a complete culture medium, DMEM supplemented with 10 U/mL of penicillin-streptomycin, 10 mM glutamine and 10% foetal calf serum (all reagents from Sigma).

The primary human fibroblasts were cultured in 24 well plates and the culture medium (supplemented DMEM) was replaced with fresh Optimem 1 medium (Gibco BRL). The cells were irradiated in the presence, or not, of the different treatments indicated in each case (Table 4). The medium was replaced with fresh Optimem 1 medium supplemented with 0.5% foetal calf serum (FCS) and $^3$H-timidine (1 uCi/mL) was added. The cells were then incubated at 37° C. for 24 h, they were washed twice with cold phosphate buffer saline (PBS) and were fixed for 20 minutes at 4° C. with 10% trichloracetic acid (TCA). Subsequently, the TCA was removed and the cells were washed twice with cold ethanol, they were dried with air and the cells were dissolved in 0.4 M NaOH for 10 minutes at 65° C. After the plate was cooled down, 5 uL of acetic acid was added to each well and the contents were transferred to scintillation vials where they were mixed with 3 mL of scintillation fluid. Finally, the radioactivity in each vial was measured in a β radiation counter for 1 minute.

The protector activity of the compositions tested (I-1, I-2, I-3, II-1, II-2, II-3, III-1, III-2, III-3, IV-1, IV-2, IV-3, V-1, V-2, V-3, VI-1, VI-2, and VI-3) enabled the cells not only to survive but also to maintain the development of their functions. The cells irradiated with UV light lost their proliferative capacity, while the cells irradiated and then incubated with the different compositions of the invention stayed alive (>75%), being able to proliferate at levels near to those of non-irradiated cells (see Table 4, where the results of the cells treated with some of the compositions tested are shown).

TABLE 4

Proliferative capacity of human fibroblasts irradiated with UVA

| Test Conditions | % cell proliferation |
| --- | --- |
| Control − UVA | 100 |
| Control + UVA 5 J/cm2 | 10 ± 5.2 |
| Cells + I-1 (1 mg/mL) − UVA | 90 ± 2.1 |
| Cells + I-1 (1 mg/mL) + UVA 5 $J/cm^2$ | 80 ± 3.3 |
| Cells + II-2 (1 mg/mL) − UVA | 88 ± 2.1 |
| Cells + II-2 (1 mg/mL) + UVA 5 $J/cm^2$ | 75 ± 4.2 |
| Cells + IV-2 (1 mg/mL) − UVA | 95 ± 1.3 |
| Cells + IV-2 (1 mg/mL) + UVA 5 $J/cm^2$ | 78 ± 4.0 |

1.4 Effect of a Composition of the Invention on the Isomerisation of Trans-Urocanic Acid Urocanic acid (UCA) is a deaminated histidine and is an active chromophore for UVB radiation. It is localised in the stratum corneum, acting thus as a natural photoprotector reagent.

The trans-UCA isomers on the skin are photo-isomerised after the absorption of UVB photons, being transformed into cis-UCA, which is a candidate as a putative mediator of some immunosupressor effects of UV radiation (van der Molen R G, Garssen J, de Klerk A, Claaus F H, Norval M, van Loveren H, Koerten H K, Mommaas A M. Photochem. Photobiol. Sci 2002, 8: 592-596).

In an unexpected way, by irradiating t-UCA with UVA, it is isomerised to cis-UCA. This can be due to that although UCA shows a maximum absorbance at 260-270 nm in the UVC radiation range (200-280 nm), it is its absorbance in the solar range (295-400 nm; UVB/UVA) which is relevant when the photobiological consequences it initiates are taken into account.

The control sample is a solution of 0.5 mg/mL of trans-UCA in 0.025% HCl. The analysis by HPLC is carried out using a flow of 1 mL/min and a diode array detector. The stationary phase is a Phenomanex Luna 250×4.6 mm (5 um) and the mobile phase is a 10 mM ammonium phosphate buffer+0.4 mM ammonium tetrabutyl hydroxide, pH=7.2-7.5: acetonitrile (96:4 v/v). 20 uL of the trans-UCA solution are injected and is detected at 278 nm.

To study the formation of cis-UCA by HPLC, the 0.5 mg/mL of trans-UCA solution is irradiated with UVA radiation for 120 mins (UVA dose, 12 J/cm$^2$) and the appearance of the peak corresponding to cis-UCA is observed. To observe the inhibition of the isomerisation, samples of 0.5 mg/mL of trans-UCA are prepared in the presence of various concentrations (0.5, 1.0, 1.5, and 2.0 mg/mL) of the compositions tested (I-1, I-1, II-3 and V-1) and are irradiated for 120 minutes.

The results of the tests carried out are shown in Table 5 and demonstrate that the tested compositions block the isomerisation of the trans-UCA induced by 12 J/cm$^2$ of UVA light.

TABLE 5

Isomerisation of urocanic acid induced by ultraviolet A light (UVA) (%)

|  | Without treatment | 0.50 mg/mL | 1.00 mg/mL | 1.5 mg/mL | 2.00 mg/mL |
| --- | --- | --- | --- | --- | --- |
| I-1 | 100 | 73 ± 5.1 | 43 ± 4.0 | 34 ± 2.9 | 32 ± 3.5 |
| II-1 | 100 | 72 ± 4.0 | 40 ± 4.3 | 34 ± 3.8 | 33 ± 3.2 |
| III-3 | 100 | 68 ± 3.8 | 38 ± 3.2 | 32 ± 4.2 | 29 ± 3.9 |
| V-1 | 100 | 65 ± 4.1 | 35 ± 3.8 | 30 ± 2.6 | 26 ± 2.7 |

1.5 Inhibition of the Immunosuppressor Effect of Ultraviolet Radiation in a Mouse Model with Hypersensitivity to Contact with Oxazolone As is known, UV radiation is capable of inducing a state of immunosuppression of the immune response. For example, when in an mouse experimental model, the mice are exposed to small sensitising molecules, such as oxazolone, and days later they are exposed to the same molecule, the mice suffer a strong immune reaction induced by an inflammatory infiltrate. When these animals are irradiated with an ultraviolet lamp in the location of the first application, the characteristic immune response is not produced.

The inventors have tested the immunosupressor effect of UV radiation in a mouse model of hypersensitivity to contact with oxazolone (CD1 mice, Charles River Laboratories, Barcelona, Spain) with different compositions provided by this invention (I-1 and V-3), observing that, when these compositions are administered orally, the mice are, surprisingly, protected from the immunosuppressor effect of UV radiation.

The CD1 mice (40 mice) were adapted at the site in temperature controlled (22° C.) conditions and a relative humidity between 50-70% and with alternative light/dark cycles every 12 hours, and were split into the groups shown in Table 6. Briefly, the control group of mice were given water and were not subjected to UVB radiation and oxazolone was not applied on them. These mice did not have any immune or inflammatory reaction. The group assigned as the positive control consisted of a group of mice which were treated with water and had oxazolone applied topically, without being exposed at any time to UVB radiation. These mice developed a strong inflammatory reaction in the oxazolone application area. The group assigned as the negative control were treated with water, and oxazolone was applied primarily in the area exposed to UVB radiation (on two occasions) and subsequently it was applied again in the ear pavilion. This negative control group presented with a significant inhibition of the inflammatory response. Finally, the group of mice treated orally with the two test compositions of the invention, (I-1 and V-3), were irradiated with UVB and oxazolone was applied on them both in area of exposure (on two occasions) and subsequently in the ear pavilion similar to the negative control group, unexpectedly, the groups treated with the compositions of the invention had an immune response close to that of the positive control group.

TABLE 6

| Group | UVB Radiation | Application of oxazolone | Oral Treatment |
| --- | --- | --- | --- |
| Control mice | Yes | No | Water |
| Positive control | No | Yes | Water |
| Negative control (irradiated) | Yes | Yes | Water |
| Mice with I-1 | Yes | Yes | 8 + 8 mg/kg* |
| Mice with V-3 | Yes | Yes | 8 + 8 mg/kg* |

*Compositions I-1 and V-3 were administered orally at 48 hours, 24 hours and half an hour before giving the second UVB radiation to the mice and 24 hours before and just after applying the oxazolone for the second time.

The radiation conditions were those described by Winder et al (Einder C V, Wax J, Burr V, Bean M and Rosiere C E. A study of Pharmacological influences on ultraviolet erythema in guinea pigs. Arch. Int. Pharmacodyn. 116: 261-292, 1958) with slight modifications described by Wendy et al (Wendy J, McDonald-Gibson S A, Saed S A, and Schneider. The local antinoceptive and topical anti-inflammatory effects of propyl gallate in rodents. Br. J. Pharmacol. 58: 573-581, 1978).

The animals were protected from ultraviolet light by covering them with a sheet of aluminium in which an opening of 1×1 cm was made over the abdomen. They were placed 8 cm from the UVB lamp with a UVC filter and were irradiated twice, with an interval of 24 hours.

The animals were treated orally with the product and, with water in the case of the control mice at 48 hours, 24 hours and half an hour before the second exposure to ultraviolet radiation. After the irradiations, a solution of 2% oxazolone in acetone was applied and they were again administered with the product. The animals then remained in their cages for 7 days. On the seventh day of the second application of oxazolone, the thickness of the ears were determined and a third dose of 2% oxazolone was applied to both ear pavilions. On the following day the thickness of the right ear was measured (Table 7) and the animal was sacrificed. The two ear pavilions were extirpated and were weighed (Table 8) on a precision balance. The statistical significance was evaluated using the Student t test.

The results displayed in Tables 7 and 8 show that compositions I-1 and V-3 exercise an unexpected photoprotector effect by inhibition of the immunosuppressor effect induced by ultraviolet radiation in this mouse of hypersensitivity by contact with oxazolone.

TABLE 7

Effect on the hypersensitivity reaction by contact. Results expressed as changes in thickness of the ear pavilion due to the effect of the inflammatory reaction to oxazolone in the sensitised mouse.

| GROUP | % Δ Final-initial thickness | % recovery vs. negative control (irradiated) |
|---|---|---|
| Blank | 18.8 ± 6.58 | — |
| Positive control | +148.9 ± 19.66 | — |
| Negative control (irradiated) | +70.85 ± 19.66 | — |
| Treated with I-1 | +251.7 ± 47.06 | +231.74 |
| Treated with V-3 | +181.8 ± 34.21 | +142.23 |

\* $P < .05$ compared to the negative control.

TABLE 8

Effect on the hypersensitivity reaction by contact. Results expressed as changes in the weight of the ear pavilion due to an effect of the inflammatory reaction to oxazolone in a sensitised mouse.

| GROUP | % Δ Final-initial weight | % recovery vs. negative control (irradiated) |
|---|---|---|
| Blank | 171.08 ± 6.65 | — |
| Positive control | 311.00 ± 12.60 | — |
| Negative control (irradiated) | 184.54 ± 24.91 | — |
| Treated with I-1 | 263.57 ± 21.03 | 62.49 |
| Treated with V-3 | 273.02 ± 22.53 | 69.90 |

\* $P < .05$ compared to the negative control.

What is claimed and desired to be secured by Letters Patent is as follows:

1. A composition to protect the skin from ultraviolet radiation for topical or oral administration, comprising:
    an amount of component A, wherein component A is
    (i) a mixture of 3,4-dihydroxycinnamic acid and 3-methoxy-4-hydroxycinnamic acid; and
    (ii) at least one selected compound selected from the group consisting of 3,4-dihydroxybenzoic acid and 3-methoxy-4-hydroxybenzoic acid;
    an amount of component B, wherein component B is quinic acid;
    an amount of component C, wherein component C is (1E, 6E)-1,7-bis(3,4-dihydroxy-phenyl)-1,6-heptadiene-3,5-dione and the amount of component C is between about 1% and about 5% by weight;
    an amount of component D, wherein component D is at least one free monosaccharide and the amount of component D is from between about 30% and about 84% by weight;
    an amount of component E, wherein component E is citric acid and the amount of component E is from between about 5% and about 20% by weight; and
    an amount of component F, wherein component F is selected from a group consisting of ascorbic acid, water soluble derivatives of tocopherol and mixtures thereof and the amount of component F is from between about 5% and about 15% by weight; wherein
    the amount of component A in combination with component B is from between about 5% and about 30% by weight; and wherein
    a ratio of the amount of component A to the amount of component B is from between about 1:1 and about 10:1 by weight.

2. The composition according to claim 1, wherein (i) and (ii) of component A are present in a molar ratio of between 0.5 and 2.

3. The composition according to claim 1, where component D is glucose.

4. The composition according to claim 1, wherein the composition is a solid.

5. The composition according to claim 1, wherein the composition is a liquid.

6. The composition according to claim 5, wherein the composition is an aqueous solution with a pH of between about 4.8 and about 6.8.

7. The composition according to claim 6, wherein the pH between about 5 and about 6.5.

\* \* \* \* \*